United States Patent
Dam-Huisman

(10) Patent No.: US 12,248,238 B2
(45) Date of Patent: Mar. 11, 2025

(54) LIGHT SOURCE FOR OPHTHALMIC APPLICATIONS

(71) Applicant: Crea IP B.V., Vierpolders (NL)

(72) Inventor: Adriaantje Coliene Dam-Huisman, Delfgauw (NL)

(73) Assignee: Crea IP B.V., Vierpolders (NL)

( * ) Notice: Subject to any disclaimer, the term of this patent is extended or adjusted under 35 U.S.C. 154(b) by 110 days.

(21) Appl. No.: 17/418,285

(22) PCT Filed: Dec. 19, 2019

(86) PCT No.: PCT/NL2019/050859
§ 371 (c)(1),
(2) Date: Jun. 25, 2021

(87) PCT Pub. No.: WO2020/139084
PCT Pub. Date: Jul. 2, 2020

(65) Prior Publication Data
US 2022/0026791 A1  Jan. 27, 2022

(30) Foreign Application Priority Data
Dec. 28, 2018  (NL) .................................... 2022322

(51) Int. Cl.
*G03B 21/20* (2006.01)
*A61F 9/008* (2006.01)
*G03B 33/12* (2006.01)

(52) U.S. Cl.
CPC ............ *G03B 21/204* (2013.01); *A61F 9/008* (2013.01); *G03B 33/12* (2013.01)

(58) Field of Classification Search
None
See application file for complete search history.

(56) References Cited

U.S. PATENT DOCUMENTS 6,193,401 B1 * 2/2001 Girkin .................. G02B 5/1876
362/555
10,036,544 B1 * 7/2018 Shum ...................... F21V 29/74
(Continued)

FOREIGN PATENT DOCUMENTS

DE  10127014 A1 * 12/2002 ............. H01S 3/067
JP  2001-511908 A  8/2001
(Continued)

*Primary Examiner* — Bao-Luan Q Le
*Assistant Examiner* — Danell L Owens
(74) *Attorney, Agent, or Firm* — N.V. Nederlandsch Octrooibureau

(57) ABSTRACT

A light source for providing a light beam to an ophthalmic instrument with a predetermined spectral content, with a first light source device (1) for providing a first beam of light (9a) along a first optical axis and with a radiation opening angle ($\alpha$). A mirror body (6) has a mirror aperture (6a) aligned with the first optical axis for allowing the first beam of light (9a) to partially pass, and a mirror surface (6b) adjacent to the mirror aperture (6a) for directing radiation from the first beam of light (9a) back to the layer of wavelength conversion material (1a). Also, a second light source device (7) may be present for providing a second beam of light (9a) along a second optical axis, and a dichroic mirror (3) for combining the first beam of light (9a) and the second beam of light (9b) into a combined beam of light (9c).

20 Claims, 1 Drawing Sheet

(56) References Cited

U.S. PATENT DOCUMENTS

Figure 1:
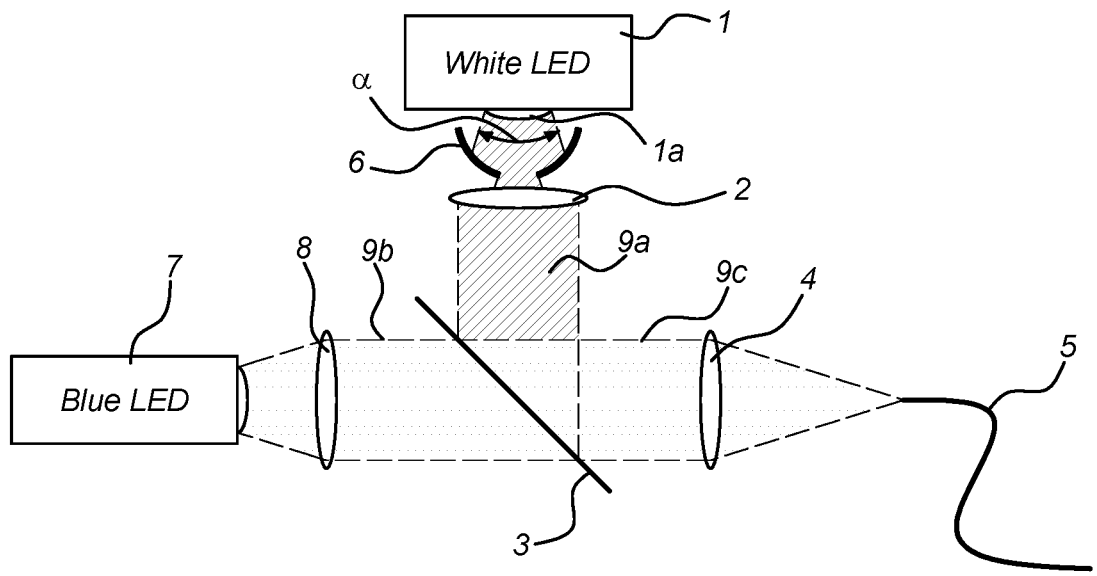

| | | | |
|---|---|---|---|
| 10,094,536 B1 | 10/2018 | Rousseau et al. | |
| 2004/0233664 A1* | 11/2004 | Beeson | G02B 19/0061 |
| | | | 362/240 |
| 2012/0051042 A1* | 3/2012 | Artsyukhovich | A61B 3/0008 |
| | | | 362/231 |
| 2013/0329448 A1* | 12/2013 | Franz | F21V 13/02 |
| | | | 362/555 |
| 2014/0022512 A1* | 1/2014 | Li | G02B 6/29337 |
| | | | 353/31 |
| 2016/0274301 A1* | 9/2016 | Mastro | G02B 6/1225 |
| 2017/0328540 A1 | 11/2017 | Paul et al. | |
| 2019/0346112 A1* | 11/2019 | Doric | H01S 5/02438 |

FOREIGN PATENT DOCUMENTS

| | | | |
|---|---|---|---|
| JP | 2004213006 A * | 7/2004 | G02B 5/1814 |
| JP | 2014-530665 A | 11/2014 | |
| JP | 2016-12556 A | 1/2016 | |
| JP | 2017-076492 A | 4/2017 | |
| KR | 649762 B1 * | 11/2006 | |
| WO | 2018/038900 A1 | 3/2018 | |

* cited by examiner

LIGHT SOURCE FOR OPHTHALMIC APPLICATIONS

FIELD OF THE INVENTION

The present invention relates to a light source for providing a light beam to an ophthalmic instrument, the light beam having a predetermined spectral content, the light source comprising a first light source device for providing a first beam of light along a first optical axis and with a radiation opening angle, the first light source device comprising a layer of wavelength conversion material which during operation is exposed to exciting radiation originating from the first light source device to produce the first beam of light.

BACKGROUND ART

International patent publication WO2012/116733 discloses a lighting apparatus which combines yellow light and blue light into a light beam which can be coupled into an optical fiber. The yellow light is obtained by irradiating a phosphor element with exciting light originating from a light source, e.g. a blue laser diode array. The structure uses a dichroic mirror to guide the exciting light beam to the phosphor element, and to combine light from a blue light source (e.g. a LED) with the phosphor element converted yellow light.

US patent publication US2015/069430 discloses a phosphor-converted light emitting device having a light emitting diode (LED) on a substrate. A wavelength conversion material is in optical communication with the LED. According to another embodiment of the phosphor-converted light emitting device, the LED comprises a mirror layer on one or more sidewalls thereof for reducing light leakage through the sidewalls.

US patent publication US2018/0266658 discloses a pumped fluorescent light source that includes a parabolic mirror positioned to focus pumping light from one or more (e.g. five) pump sources on a front surface of a fluorescent body. The parabolic mirror is circular or annular in profile having an aperture for extracting the emitted output beam from the fluorescent body. The parabolic mirror is arranged to reflect radiation received from the pump sources onto a separate fluorescent body.

US patent publication US2017/0328540 discloses a lighting device with excitation light source(s) for emitting primary radiation which is utilizable as excitation light and a wavelength conversion assembly for converting the excitation light into light in a spectral range which differs from the excitation light (conversion light). The structure and operation is optimized to allow alternate use of the excitation light and conversion light, by using a reflection element(s) and a dichroic mirror.

SUMMARY OF THE INVENTION

The present invention seeks to provide a light source that can be readily applied in ophthalmic applications, e.g. as a light source for an optical fibre connected to an instrument delivering optical radiation to the eye during surgery, such as light probes, chandeliers, etc.

According to the present invention, a light source as defined above is provided, further comprising a mirror body having a mirror aperture, the mirror aperture being centred on the first optical axis for allowing the first beam of light to partially pass, and a mirror surface adjacent to the mirror aperture for directing radiation from the first beam of light back to the layer of wavelength conversion material. This allows the part of the first beam of light not passing through the mirror aperture to be reflected back to the layer of wavelength conversion material, thus adding to the efficiency of wavelength conversion and/or secondary reflection from the wavelength conversion material through the mirror aperture.

SHORT DESCRIPTION OF DRAWINGS

Figure 2:
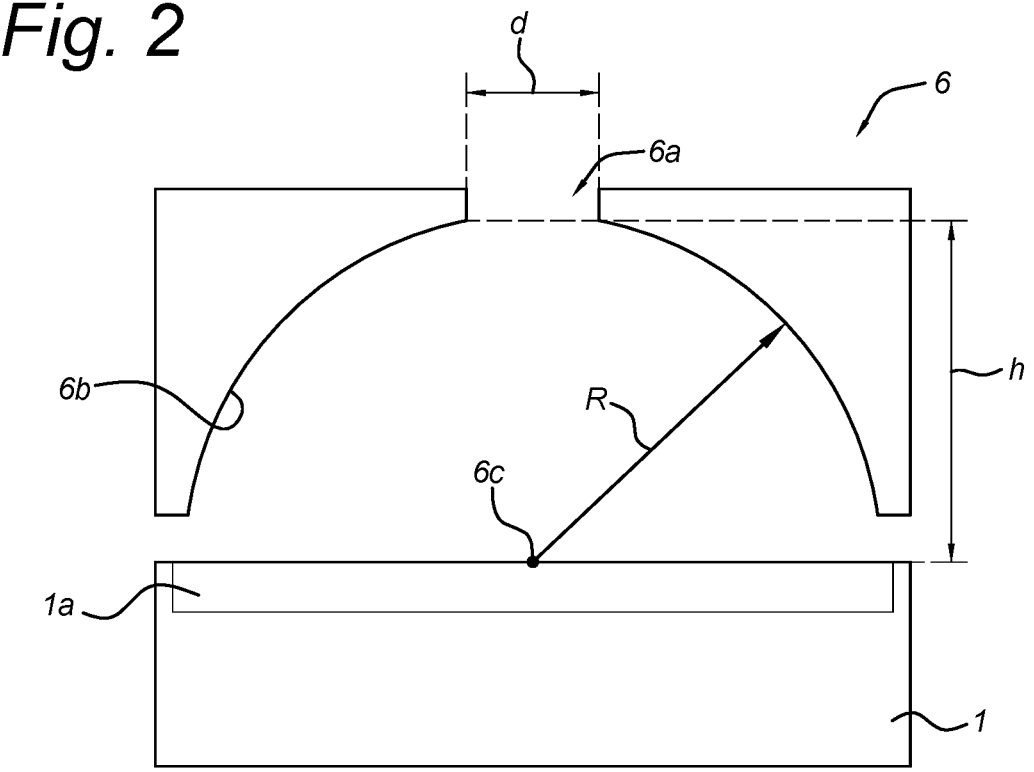

The present invention will be discussed in more detail below, with reference to the attached drawings, in which FIG. 1 shows a schematic cross sectional view of a light source according to an embodiment of the present invention; and FIG. 2 shows a cross sectional view of an embodiment of a mirror useable in a light source according to the present invention.

DESCRIPTION OF EMBODIMENTS

Ophthalmic surgical procedures can put requirements on desirable lighting conditions, e.g. to required lighting strength (power) and spectral content. According to the present invention embodiments, a light source is provided which can couple radiation into an optical fiber 5 (glass or plastic optical fiber). The optical fiber 5 can be coupled to a further (ophthalmic) instrument to pass on the radiation into the eye. All embodiments disclosed herein provide the advantage that, compared to prior art systems, it is possible to couple more light power into a small(er) diameter fiber 5.

FIG. 1 shows a schematic cross sectional view of a light source, able to couple light into a receiving end of an optical fiber 5. To achieve this, a first light source device 1 is provided, e.g. as shown in the exemplary embodiments in the form of a white LED, which has a layer of wavelength conversion material 1a. It is noted that in the embodiment shown, the layer of wavelength conversion material 1a is directly attached to a radiation emitting surface of the first light source device 1. In specific embodiments, the wavelength conversion material is a luminescent material, or even a fluorescent material. In a practical implementation, the wavelength conversion material comprises a suitable phosphor based composition. The first light source device 1 emits radiation (e.g. from a 1×1 mm active surface) within a radiation opening angle α around a first optical axis (i.e. the light is emitted in a first direction). Furthermore, a second light source device 7 is provided, e.g. as shown in the form of a blue LED. A first lens 2 (or lens array) modifies the radiation from the first light source device 1 (i.e. emanating from the top of the layer of wavelength conversion material 1a) into a first beam of light 9a, and a second lens 8 (or lens array) modifies the radiation from the second light source device 7 into a second beam of light 9b. A dichroic mirror 3 is present which reflects the light originating from the first light source device 1, and passes the light originating from the second light source device 7, effectively resulting a combined beam of light 9c. This combined beam of light 9c can then be passed through a collimator 4 (e.g. in the form of a lens or a lens array) and focussed on a receiving end of the optical fiber 5.

In a group of embodiments, the first light source device 1 has an (optical) output of more than 290 lumen, e.g. 640 lumen. This allows the light source to have higher optical power output than existing light sources, especially advantageous when the optical power is output and coupled into the optical fiber 5, as discussed above. The high optical output power from the first light source device 1 can be obtained by operating the first light source device 1 with a current of 1000 mA (obtaining an output of 290 lumen), up to even 3000 mA (obtaining an output of 640 lumen).

In accordance with present invention embodiments, a mirror body 6 is provided which is arranged to interact with light radiation originating from the first light source device 1. As shown in the cross sectional view of an exemplary embodiment of the mirror body 6 of FIG. 2, the mirror body 6 has an opening aperture 6a, having a diameter d, and a mirror surface 6b. The aperture 6a is present in the mirror surface 6b at a height h from the layer of wavelength conversion material 1a, the height h having a value of between 5 and 50 mm, e.g. equal to 10 mm. In the embodiment shown in FIG. 2, the mirror surface 6b is dome shaped (e.g. hemispherical), and has a radius R from a focal point 6c, or in other words, the mirror surface 6b has an inner surface with a radius R, e.g. between 5 and 50 mm, e.g. equal to 10 mm. The focal point 6c is thus positioned on top of, or within the layer of wavelength conversion material 1a. This mirror body 6 is aligned with the radiation exiting from the layer of wavelength conversion material of the first light source device, such that the radiation exiting through the aperture 6a impinges on the first lens 2.

According to an embodiment of the present invention, a light source is provided for providing a light beam to an ophthalmic instrument, the light beam having a predetermined spectral content. The light source comprises a first light source device 1 for providing a first beam of light 9a along a first optical axis and with a radiation opening angle α, and the first light source device 1 comprises a layer of wavelength conversion material e.g. in the form of a phosphor layer 1a which during operation is exposed to exciting radiation originating from the first light source device 1 to produce the first beam of light 9a. A mirror body 6 has a mirror aperture 6a, the mirror aperture 6a being centred on (or aligned with) the first optical axis for allowing the first beam of light 9a to partially pass, and a mirror surface 6b adjacent to the mirror aperture 6a for directing radiation from the first beam of light 9a back to the layer of wavelength conversion material 1a. As a result, radiation not exiting the mirror body 6 through the mirror aperture 6a is reflected back towards the layer of wavelength conversion material 1a. In the radiation reflected back, the spectral content will still include some blue light radiation, which with a high degree of certainty will interact with the layer of wavelength conversion material 1a to provide additional optical energy, usually radiating from the layer 1a, and thus enhancing the output of the first light source device. In a further embodiment, therefore, the first light source device 1 emits light having a spectral content including blue radiation. Furthermore, the layer of wavelength conversion material 1a will have optical reflective properties, which will also re-reflect part of the reflected radiation, possibly then exiting through the aperture 6a. In an even further embodiment of the present invention, therefore, the layer of wavelength conversion material 1a is reflective, e.g. reflective in general for white light. It is noted that it if the first light source device 1 is a laser or LED based light source, it is counterintuitive to reflect radiation back to the first light source device 1 for reasons of thermal management of the first light source device 1.

In a further embodiment of the present invention light source, the mirror surface 6b has a focal point 6c on (or even in) the layer of wavelength conversion material 1a. This will ensure that all light radiation not exiting the mirror body 6 through the mirror aperture 6a is reflected back in or onto the layer of wavelength conversion material 1a, increasing the amount of light radiation converted by or reflecting from the wavelength conversion material.

In practical implementations, the first light source device 1 is e.g. a white light emitting LED, having a frontal light emitting surface with a diameter of e.g. 1 mm (or with a square surface of 1×1 mm), and a total included angle (i.e. the total angle that includes 90% of the total luminous flux) of about 140-150 degrees. This could correspond to a viewing angle (off axis angle from emitter centreline where the luminous intensity is 50% of the peak value) of about 110-120 degrees.

In a further embodiment, the mirror aperture 6a has a diameter d of between 3 and 10 mm, e.g. 6 mm. This, in combination with proper dimensions of the first lens 2 (e.g. 16 mm diameter) will ensure a large part of the emitted radiation will be transformed into the first beam of light 9a.

The mirror surface 6b has an inner surface with a hyperbolic cross section in an even further embodiment. In even further alternative embodiments, the inner surface has an elliptic shape. These embodiments allow to select dimensions of the entire light source in an efficient manner in view of the light sources 1, 7 and lenses 2, 8 being used.

In a further group of embodiments, which has already been described by reference to FIG. 1 above, the light source further comprises a second light source device 7 for providing a second beam of light 9b along a second optical axis, and a dichroic mirror 3 for combining the first beam of light 9a and the second beam of light 9b into a combined beam of light 9c. This allows to more precisely obtain a desired spectral content for specific (ophthalmic) applications, e.g. by selecting the first and second light source device 1, 7 having specific optical properties, and/or by selecting a dichroic mirror 3 with specific optical properties. E.g., in a further embodiments, the second light source device 7 is a LED emitting blue light. In an even further embodiment, the second light source device 7 is a LED provided with a dome lens. This allows to optimize the dimensions of second lens 8 in order to have a proper combination of radiation from the first light source device 1 and second light source device 7 at the dichroic mirror 3.

Furthermore, the light source in a further embodiment further comprises a collimator 4 (e.g. a lens or lens array) and an optical fiber 5, the collimator 4 being arranged to receive the combined beam of light 9c from the dichroic mirror 3 and to couple the combined beam of light 9c into a receiving end surface of the optical fiber 5. This embodiment allows to couple light with a high intensity into the optical fiber 5, which in certain (ophthalmic) applications is required or beneficial. In a further embodiment, the collimator 4 comprises an achromatic optical system (e.g. a two-lens system) having a numerical aperture NA of at least 0.55, e.g. equal to 0.63. The high NA allows to effectively optimize both the capture of radiation (the combined beam of light 9c) and the focussing thereof onto the receiving end of fiber 5.

In a first exemplary embodiment, the collimator 4 comprises a lens array having a diameter of 14 mm. The lens array has a first lens of a material with a refractive index of 1.903659 and a center thickness of 4.2 mm, and a second lens of a material with a refractive index of 1.963 and center thickness of 6.79 mm. The first lens has a receiving surface with a radius of about 11.3 mm. The (matching) surfaces where the first lens and second lens of the lens array meet have a radius of about 11.9 mm. The output surface of the second lens is a flat surface (no curvature).

In a second exemplary embodiment, the collimator 4 comprises lens array having a diameter of 18 mm. The lens array has a first lens of a material with a refractive index of 1.7645 and a center thickness of 8.52 mm, and a second lens of a material with a refractive index of 1.95906 and a center thickness of 3.5 mm. The first lens has a receiving surface with a radius of about 19.7 mm. The (matching) surfaces where the first lens and second lens of the lens array meet have a radius of about 11.5 mm. The output surface of the second lens has a radius of 31.1 mm.

The present invention has been described above with reference to a number of exemplary embodiments as shown in the drawings. Modifications and alternative implementations of some parts or elements are possible, and are included in the scope of protection as defined in the appended claims.

The invention claimed is:

1. A light source for providing a light beam having a predetermined spectral content to an ophthalmic instrument, the light source comprising:
    a first light source device for providing a first beam of light along a first optical axis and with a radiation opening angle, the first light source device arranged on the first optical axis and comprising
        a layer of wavelength conversion material, which during operation, is exposed to exciting radiation originating from the first light source device to produce the first beam of light, the layer of wavelength conversion material attached to the first light source device,
    a mirror body having a mirror surface comprising a mirror aperture centered on the first optical axis, wherein a part of the first beam of light exits the mirror body through the mirror aperture and a remaining part of the first beam of light contacts the mirror surface and is reflected back to the layer of wavelength conversion material,
    a second light source device for providing a second beam of light along a second optical axis,
    a dichroic mirror adapted to combine the first beam of light and the second beam of light into a combined beam of light, wherein the dichroic mirror is arranged to reflect light originating from the first light source and to transmit light originating from the second light source, and
    an achromatic optical system having a numerical aperture of at least 0.55 and comprising a first lens with a first refractive index and a second lens with a second refractive index, wherein the first lens has a receiving surface with a first radius, a contact surface between the first and second lenses has a shared radius which is larger than the first radius, and the second lens has an output surface that is flat.

2. The light source according to claim 1, wherein the layer of wavelength conversion material is directly attached to a radiation emitting surface of the first light source device.

3. The light source according to claim 1, wherein the mirror aperture is positioned at a height h from the layer of wavelength conversion material.

4. The light source according to claim 1, wherein the mirror surface has a focal point on the layer of wavelength conversion material.

5. The light source according to claim 1, wherein the mirror aperture has a diameter d of between 3 and 10 mm.

6. The light source according to claim 1, wherein the mirror surface is dome shaped.

7. The light source according to claim 1, wherein the mirror surface has an inner surface with a hyperbolic cross section.

8. The light source according to claim 1, wherein the first light source device emits light having a spectral content including blue radiation.

9. The light source according to claim 1, wherein the wavelength conversion material is a luminescent material.

10. The light source according to claim 1, wherein the layer of wavelength conversion material is reflective.

11. The light source according to claim 1, further comprising an optical fiber having a receiving end surface onto which the combined beam of light from the dichroic mirror is coupled by the achromatic optical system.

12. The light source according to claim 1, wherein the second light source device is a LED provided with a dome lens.

13. The light source according to claim 5, wherein the mirror aperture has a diameter d of 6 mm.

14. The light source according to claim 1, wherein the second light source device is an LED emitting blue light.

15. The light source according to claim 1, wherein the layer of wavelength conversion material is arranged in between the first light source device and the mirror body.

16. The light source according to claim 1, wherein the first light source has an output of from 290 to 640 lumen.

17. A light source for providing a light beam having a predetermined spectral content to an ophthalmic instrument, the light source comprising:
    a first light source device for providing a first beam of light along a first optical axis and with a radiation opening angle, the first light source device arranged on the first optical axis and comprising
        a layer of wavelength conversion material, which during operation, is exposed to exciting radiation originating from the first light source device to produce the first beam of light, the layer of wavelength conversion material attached to the first light source device,
    a mirror body having a mirror surface comprising a mirror aperture centered on the first optical axis, wherein a part of the first beam of light exits the mirror body through the mirror aperture and a remaining part of the first beam of light contacts the mirror surface and is reflected back to the layer of wavelength conversion material,
    a second light source device for providing a second beam of light along a second optical axis,
    a dichroic mirror adapted to combine the first beam of light and the second beam of light into a combined beam of light, wherein the dichroic mirror is arranged to reflect light originating from the first light source and to transmit light originating from the second light source, and
    an achromatic optical system having a numerical aperture of at least 0.55 and comprising a first lens with a first refractive index and a second lens with a second refractive index, wherein the first lens has a receiving surface with a first radius, a contact surface between the first and second lenses has a shared radius which is smaller than the first radius, and the second lens has an output surface with a second radius that is larger than the first radius.

18. The light source according to claim 17, further comprising an optical fiber having a receiving end surface onto which the combined beam of light from the dichroic mirror is coupled by the achromatic optical system.

19. The light source according to claim 17, wherein the mirror surface has a focal point on the layer of wavelength conversion material, and the wavelength conversion material is a luminescent material and/or is reflective.

20. The light source according to claim 17, wherein the first light source device emits light having a spectral content including blue radiation.

\* \* \* \* \*